United States Patent [19]

Ouchi et al.

[11] Patent Number: 4,497,550
[45] Date of Patent: Feb. 5, 1985

[54] DEVICE FOR PREVENTING THE OBSERVING OBJECTIVE LENS WINDOW OF AN ENDOSCOPE FROM COLLECTING MOISTURE

[75] Inventors: Teruo Ouchi; Kiyoshi Chikashige, both of Saitama; Hirohisa Ueda, Tokyo, all of Japan

[73] Assignee: Kabushiki Kaisha Medos Kenkyusho, Tokyo, Japan

[21] Appl. No.: 360,086

[22] Filed: Mar. 19, 1982

Related U.S. Application Data

[63] Continuation of Ser. No. 132,713, Mar. 21, 1980, abandoned.

[30] Foreign Application Priority Data

Apr. 23, 1979 [JP] Japan .......................... 54/54984[U]

[51] Int. Cl.³ .......................... A61B 1/00; F15B 1/00
[52] U.S. Cl. ...................................... 350/584; 15/246; 137/627.5; 137/561 R
[58] Field of Search ...................... 350/63; 128/6, 5, 4

[56] References Cited

U.S. PATENT DOCUMENTS 3,726,272 4/1973 Fukami et al. ..................... 128/6

3,903,877 9/1975 Terada ................................. 350/63

FOREIGN PATENT DOCUMENTS 48-34638 10/1973 Japan .................................. 128/6

Primary Examiner—Jon W. Henry
Attorney, Agent, or Firm—Sughrue, Mion, Zinn, Macpeak, and Seas

[57] ABSTRACT

A device for preventing the observing objective lens window of an endoscope from collecting moisture by directing a small flow of air over the front surface of the observing objective lens window to form a layer of air which has the same temperature as the ambient atmosphere thereby stabilizing the temperature of the window. A control valve is provided which shuts off the flow of air in the event that the pressure within the body cavity in which the endoscope is inserted becomes too high due to the flow of air. A first embodiment of the control valve includes a cylinder and piston arrangement in which at a first position of the piston air is allowed to flow through the tube to the endoscope end. At a second position of the piston, air is vented directly to the atmosphere. In a second embodiment, a lateral hole is provided in the piston with the area of the hole and hence flow of air controlled by a screw the position of which determines the area of the lateral aperture.

6 Claims, 3 Drawing Figures

DEVICE FOR PREVENTING THE OBSERVING OBJECTIVE LENS WINDOW OF AN ENDOSCOPE FROM COLLECTING MOISTURE

This is a continuation of application Ser. No. 132,713, filed Mar. 21, 1980 (now abandoned).

BACKGROUND OF THE INVENTION

To examine a body cavity with an endoscope, the flexible pipe of the endoscope is inserted into the body cavity. Since the normal body temperature is about 36° C., the temperature of the body cavity is usually higher than the temperature of the outside air. The humidity in a body cavity is usually very high, about 100%. On the other hand, the temperature of the flexible pipe of the endoscope before it is inserted into the body cavity is substantially that of the ambient air. Accordingly, when the flexible pipe is inserted into the body cavity, its temperature increases. Because of the initial temperature difference, an observing objective lens window provided at the end of the flexible pipe collects moisture.

During observation of the body cavity with the endoscope, sometimes it is necessary to supply air into the body cavity to expand a part of the body cavity or to supply water to the observing objective lens window to remove foreign matter therefrom. In such a case, as the end portion of the flexible pipe of the endoscope is cooled by the air or water, the window collects moisture.

When the objective lens window collects moisture as described above, it is difficult to observe the body cavity which may therefore result in an erroneous diagnosis. Accordingly, it is necessary to carry out diagnostic observation exceedingly carefully so that it takes a relatively long time for adequate observation. Undoubtedly, this inflicts pain on the patient and the operator will tire. Thus, it is necessary to prevent the objective lens window from collecting moisture. Otherwise, undesirable conditions as described above may result. Especially, in photographing the body cavity, moisture collection on the objective lens window must be prevented.

In order to prevent the objective lens window from collecting moisture, heretofore a technique was employed in which, before the endoscope is used, the objective lens window was coated with a hydrophilic lens cleaner such as a liquidstate hydrophilic cleaner or a solid soap. However, the conventional technique is still disadvantageous in the following points. The window surface is covered with the hydrophilic lens cleaner at all times. However, such a solid lens cleaner becomes liquified due to the relatively high temperature of the body cavity and a film layer forms on the objective lens. When observation is made through the film layer, which tends to be wavy, the image observed through the objective lens is distored. That is, the optical performance of the objective lens is significantly lowered with the result that it is rather difficult to make an accurate diagnostic observation of an affected part.

Moreover, the service life of the lens cleaner is reduced and the effect of the lens cleaner is lowered by supplying air or water into the body cavity. As a result, the objective lens window again will collect moisture. Thus, the above-described conventional technique is not entirely suitable for an examination of a body cavity which requires a relatively long time.

Water repellent cleaner has also been employed to coat the objective lens window. The use of a water repellent cleaner is also disadvantageous similar to the case of a hydrophilic lens cleaner. Yet further, a technique utilizing a dry system lens cleaner has also been known in the art. However, that technique involves a problem in that the objective lens window still collects moisture due to the above-described temperature difference.

Accordingly, an object of the present invention is to provide a device for preventing the observing objective lens window from collecting moisture in which the above-described drawbacks accompanying conventional techniques utilizing lens cleaners have been eliminated.

SUMMARY OF THE INVENTION

This, as well as other objects of the invention, are met by a device for preventing the observing objective lens window of an endoscope from collecting moisture including means for providing a small flow of air over the front surface of the observing objective lens windows at all times so as to form a layer of air on the front surface of the observing lens window. The flow of air is preferably provided by a fluid supplying tube disposed through an end member of the endoscope which has an aperture disposed so as to direct air over the front surface of the observing objective lens window. There is also preferably provided a control valve which will shut off the flow of air in the event that the pressure within the body cavity becomes too high due to the presence of the air flow. In one embodiment of the control valve, a piston having a longitudinal opening is disposed in a cylinder in a main air passage with apertures formed in the piston so that at a first position of the piston air can flow through the tube whereas at a second position of the piston the air is vented to the atmosphere. A bypass tube including a pressure regulator valve extends around the cylinder and piston. In another embodiment, the piston is provided with a lateral opening and a screw the position of which controls the area of the lateral opening. A blow-by section is provided at the lower end of the piston.

DESCRIPTION OF THE PREFERRED EMBODIMENTS

The preferred embodiments of the invention will be described with reference to the accompanying drawings.

Figure 1:
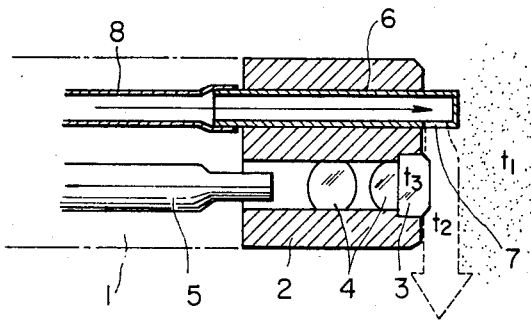
FIG. 1 is a longitudinal sectional view showing essential components of a preferred embodiment of a device for preventing the observing objective lens window of an endoscope from collecting moisture according to the invention.

FIG. 1 is a longitudinal sectional view showing the essential components of a preferred embodiment of a device constructed according to the present invention. A window is formed in the end face of a metal member 2 provided at the end of an endoscope flexible pipe 1. The window is covered with a protective glass 3 and an objective lens system 4 is arranged in the window thus forming an observing objective lens section. The observing objective lens section is coupled through an optical fiber bundle 5 to an endoscope manual operating section.

A tube 6 is disposed in the metal member 2. The tube 6 is used to supply air and/or water. The tube 6 has a jetting outlet 7 opening at the end face of the metal member 2. An air and water supplying tube 8 is connected between the manual operating section and the tube 6.

Figure 2:
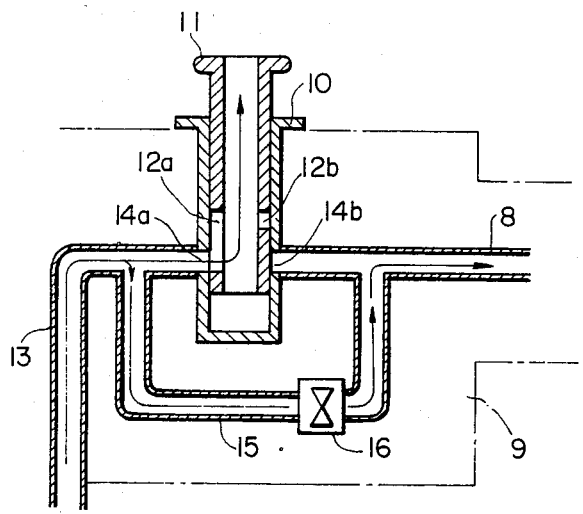
FIGS. 2 and 3 are longitudinal sectional views showing essential components of manual operating sections used with the device of FIG. 1.

FIG. 2 is a longitudinal sectional view of the essential components of the manual operating section showing an example of an air supply control section in the device constructed according to the invention. An air and water supply control valve 10 is provided in a manual operating section body 9. One end 14a of a tube 13 connected to an air pump (not shown) opens into the wall of the cylinder of the control valve 10 while the other end 14b of the tube 8 also opens into the wall of the cylinder. That is, the control valve 10 is so designed that, as the piston 11 is moved vertically, apertures 12a and 12b formed in the wall of the piston 11 reach the levels of the end 14a of the tube 13 and the end 14b of the tube 8 and then to move beyond the ends 14a and 14b.

A bypass tube 15 for the air and water supply control valve 10 is connected between the tube 13 and the tube 8. A pressure valve 16 for regulating the quantity of air is disposed in the bypass tube 15.

Figure 3:
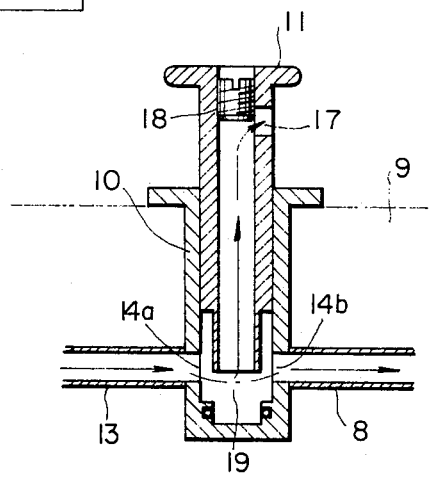

FIG. 3 is a longitudinal sectional view of essential components of the manual operating section showing another example of the air supply control section in a device constructed according to the invention. In FIG. 3, those components which have been previously described with reference to FIG. 2 are therefore similarly numbered. In this example, the hollow piston 11 is provided with an opening 17 which communicates with the atmosphere and an adjusting screw 18 disposed in the piston 11 in such a manner that it can vary the area of the opening 17. Furthermore, a blow-by section 19 is provided in the cylinder of the air and water supply control valve 10 which connects the tube 13 to the tube 8 through the hollow cylinder of the piston 11.

In the device thus constructed, compressed air is delivered by the air pump to the air and water supply control valve 10 through the tube 13. In the structure shown in FIG. 2, when the piston 11 is lifted, the aperture 12a and the pipe end 14a, which open and close the air supply passage, are brought into coincidence with each other while the aperture 12b and pipe end 14b do not coincide with each other. In this case, the air supply passage to the tube 8 is closed in the control valve 10. Under this condition, almost all the compressed air is discharged outside through an opening formed at the top of the hollow piston 11. However, a small quantity of air, typically about 10 to 50 cm$^3$/min, is delivered through the bypass tube 15 to the tube 8 under the control of the pressure valve 16. In the structure shown in FIG. 3, if the area of the opening 17 formed in the wall of the hollow piston 11 is suitably adjusted with the use of the adjusting screw 18, then the quantity of air supplied from the tube 13 is maintained in balance with the quantity of air discharged through the opening and therefore the air pressure in the blow-by section 19 is maintained at an appropriate value as a result of which the quantity of air supplied to the tube 8, which is relatively small in diameter, is made quite small.

The air thus supplied to the tube 8 is allowed to flow out of the jetting outlet 7 in the end face of the metal member 2 towards the objective lens window. The air T2 flowing out of the jetting outlet 7 spreads over the entire end face of the metal member 2 in such a manner that it covers the front surface of the protective glass 3 in the window as indicated by the thin line in FIG. 1. As a result, the objective lens window section T3 with the protective glass 3 is isolated from the gas in the body cavity by the air thus supplied.

According to the invention, a small quantity of air is supplied to the objective lens window as described above. The gas in the body cavity is saturated with water vapor because of the high temperature and high humidity present there. The temperature of the front surface of the protective glass 3 is increased when the flexible pipe of the endoscope is inserted into the body cavity. However, the temperature is decreased, such as typically to about 20° C., when it is washed with cleaning water. Thus, because of the temperature difference, the surface of the protective glass 3 would ordinarily collect moisture. However, in the case where a small amount of air is supplied through the jetting outlet 7 as described above, the surface of the protective glass 3 will not collect moisture because the air thus supplied is outside air having a temperature of about 20° C. and the air is relatively dry. Therefore a layer of low temperature air T2 is formed between the surface of the protective glass 3 in the observing objective lens window and the wet air layer in the body cavity thereby preventing the surface of the protective glass from collecting moisture.

The temperature of the protective glass 3 is increased somewhat by the body temperature when the flexible pipe of the endoscope is inserted into the body cavity although the air supplied is at the temperature of the outside air. However, with the temperature of the air supplied lower than the body temperature, it is possible to prevent the surface of the protective glass 3 from collecting moisture. The surface of the protective glass 3 will not then collect moisture because the air supplied is relatively dry and it does not become saturated due to the small temperature difference.

In the case where the endoscope in the body cavity is operated without using an air pump, the surface of the protective glass will quickly collect moisture. Even in this case, the moisture can be readily removed from the surface of the protective glass because the dry air is supplied to the surface of the protective glass causing the moisture to evaporate.

As a small quantity of air is supplied to the front of the observing objective lens window, that is, at the surface of the protective glass 3 at all times, it may be questioned whether the air thereby introduced into the body cavity will have an adverse effect upon the body cavity or whether it will adversely effect the examination thereof. However, in practice, no problem results. That is due to the fact that the quantity of air supplied per unit of time is extremely small when compared with the volume of the typical body cavity to be examined. The air supplied simply flows out of the body cavity or flows into other body parts.

With the structures of the device shown in FIGS. 2 and 3, a small quantity of air is supplied into the body cavity by delivering compressed air from the air pump under pressure control in such a manner that, when the pressure in the body cavity to be examined increases, supply of air is automatically stopped. Therefore, such an abnormal condition will never occur.

With the device according to the invention, an isolating layer of air is formed between the front surface of the observing objective lens window and the air layer in the body cavity at all times thereby preventing the window from collecting moisture. Accordingly, it is possible to observe the body cavity clearly at all times and the body cavity can be readily examined in a shorter time than was possible with prior art devices. As the objective lens surface is covered with dry air at all times, it is maintained in an optically ideal state. Accordingly, it is possible to take accurate pictures of the body cavity.

As no lens cleaner is employed in the device of the invention, the expense of coating the lens is eliminated and the potential problem that the jetting opening may become clogged during the coating operation is eliminated.

In the device of the invention in which the observing objective lens window is covered with dry air, a dry system lens cleaner having a water repelling function may be employed in combination. In this case, any tendency for foreign matter to stick the window is eliminated thereby further improving the observing conditions.

What is claimed is:

1. A device for preventing the observing objective lens window of an endoscope from collecting moisture comprising: an air source; means for providing a small flow of air over the front surface of said observing objective lens window at all times so as to form a layer of air on the front surface of said observing objective lens window; said air source comprising a control valve having a first tube, a cylinder having openings to said first tube and a piston slidably disposed in said cylinder; said piston having a center longitudinal opening and first and second apertures of different sizes disposed in said piston at positions so that for a first position of said air is allowed to flow along said first tube and for a second position of said piston air is vented to the atmosphere through said center longitudinal openings; a bypass tube around said first tube; and a pressure regulator valve disposed in said bypass tube.

2. A device for preventing the observing objective lens window of an endoscope from collecting moisture comprising: an end metal member adapted to be connected at one end thereof to an end of a flexible tube of an endoscope; an objective lens system disposed in an aperture through said metal member; an objective lens window disposed to cover said objective lens system; a source of air; a tube disposed through an aperture in said end member and being adapted to be connected to said source of air, said tube having an aperture directed toward said objective lens window for detecting a layer of air on the front surface of said objective lens window; said air source comprising a control valve having a first tube, a cylinder having openings to said first tube and a piston slidably disposed in said cylinder, said piston having a center longitudinal opening and first and second apertures of different sizes disposed in said piston at positions so that for a first position of said piston air is allowed to flow along said first tube and for a second position of said pistion air is vented to the atmosphere through said center longitudinal opening; a bypass tube around said first tube; and a pressure regulator valve disposed in said bypass tube.

3. A device for preventing the observing objective lens window of an endoscope from collecting moisture comprising: means for providing a small flow of air over the front surface of said observing objective lens window at all times so as to form a layer of air on the front surface of siad observing objective lens window; an air source comprising a control valve member having a cylinder with openings to a tube extending through an end member and a piston disposed in said cylinder; said piston having a center longitudinal opening and a lateral opening in an upper portion thereof and a screw disposed in said longitudinal opening wherein the area of siad lateral opening is variable in accordance with the position of said screw and said piston having a blow-by section formed at a lower portion thereof.

4. A device for preventing an observing objective lens window of an endoscope from collecting moisture comprising: a source of air; means for providing a continuous small flow of air from said source over the front surface of said observing objective lens window, said continuous small flow of air forming a layer of air on the front surface of said observing objective lens window isolating said front surface from the environment of the endoscope during use, and said air source comprises a control valve comprising a first tube, a cylinder having openings to said first tube and a piston slidably disposed in said cylinder, said piston having a center longitudinal opening and first and second apertures of different sizes disposed in said piston at positions so that for a first position of said piston air is allowed to flow along said first tube and for a second position of said piston air is vented to the atmosphere through said center longitudinal opening; a bypass tube around said first tube; and a pressure regulator valve disposed in said bypass tube.

5. A device for preventing an observing objective lens window of an endoscope from collecting moisture comprising: an end metal member adapted to be connected at one end thereof to an end of a flexible tube of an endoscope; an objective lens system disposed in an aperture through said metal member; an objective lens window disposed to cover said objective lens system; a source of air; a tube disposed through an aperture in said end member and being adapted to be connected to said source of air, said tube having an aperture directed toward said objective lens window; and means supplying air from said source to said tube for establishing a continuous layer of air on the front surface of said objective lens window to isolate said front surface from the environment of the endoscope during use, said source of air comprises a control valve comprising a first tube, a cylinder having openings to said first tube and a piston slidably disposed in said cylinder, said piston having a center longitudinal opening and first and second apertures of different sizes disposed in said piston at positions so that for a first position of said piston air is allowed to flow along said first tube and for a second position of said piston air is vented to the atmosphere through said first tube; and a pressure regulator valve disposed in said bypass tube.

6. A device for preventing an observing objective lens window of an endoscope from collecting moisture comprising: a source of air; means for providing a continuous small flow of air from said source over the front surface of said observing lens window, said continuous small flow of air forming a layer of air on the front surface of said observing objective lens window isolating said front surface from the environment of the endoscope during use, said source of air comprises a control valve member comprising a cylinder having openings to a tube extending through an end member and a piston disposed in said cylinder, said piston having a center longitudinal opening and a lateral opening in an upper portion thereof and a screw disposed in said longitudinal opening wherein the area of said lateral opening is variable in accordance with the position of said screw and said piston having a blow-by section formed at a lower portion thereof.

* * * * *